United States Patent [19]

Wolff et al.

[11] 4,425,360

[45] Jan. 10, 1984

[54] PHARMACOLOGICALLY ACTIVE NOVEL O-SUBSTITUTED PYRUVIC ACID OXIMES

[75] Inventors: Hans P. Wolff, Hirschberg-Grossachsen; Ruth Heerdt, Mannheim, both of Fed. Rep. of Germany; Manfred Hübner, deceased, late of Ludwigshafen, Fed. Rep. of Germany, by Dietmar Hübner, legal representative; Hans Kühnle, Weinheim; Felix H. Schmidt, Mannheim, both of Fed. Rep. of Germany

[73] Assignee: Boehringer Mannheim GmbH, Mannheim, Fed. Rep. of Germany

[21] Appl. No.: 300,076

[22] Filed: Sep. 8, 1981

[30] Foreign Application Priority Data

Sep. 26, 1980 [DE] Fed. Rep. of Germany ....... 3036281

[51] Int. Cl.$^3$ .................... A61K 31/15; C07C 131/00
[52] U.S. Cl. .................... 424/309; 560/168; 560/125; 560/35; 560/17; 560/121; 560/123; 560/124; 562/560; 562/440; 562/431; 562/503; 562/505; 562/506; 562/507; 424/316; 424/319; 424/320; 564/167; 564/162; 564/172; 564/191; 564/189; 564/190; 564/123; 564/224; 564/215; 260/501.11; 260/501.12
[58] Field of Search ............. 562/560, 440, 431, 503, 562/505, 506, 507; 560/168, 125, 35, 17, 121, 123, 124; 424/309, 319, 316, 320; 564/167, 162, 172, 191, 189, 190, 123, 224, 215; 260/501.11, 501.12

[56] References Cited

U.S. PATENT DOCUMENTS

| | | | |
|---|---|---|---|
| 3,104,258 | 9/1963 | Ferris | 562/560 |
| 3,703,113 | 9/1975 | Bradshaw et al. | 562/440 |
| 4,052,194 | 10/1977 | Wilcox | 562/560 |
| 4,060,686 | 11/1977 | Bradshaw et al. | 560/35 |
| 4,206,231 | 6/1980 | Haeckel | 560/168 |
| 4,237,305 | 12/1980 | Kamiya et al. | 560/35 |
| 4,387,104 | 6/1983 | Heerdt et al. | 562/439 |

FOREIGN PATENT DOCUMENTS 2837863 3/1980 Fed. Rep. of Germany ...... 424/309

*Primary Examiner*—James H. Reamer
*Attorney, Agent, or Firm*—Sprung, Horn, Kramer & Woods

[57] ABSTRACT

The present invention provides pyruvic acid oximes of the general formula:

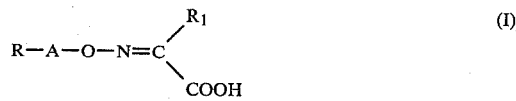

wherein R is a hydrogen atom, a $C_3$-$C_8$ cycloalkyl, $C_1$-$C_6$ alkoxy, cinnamyloxy, phenylamino, phenyl-N-alkylamino or phenylthio radical or an aryl or aryloxy radical, the aryl moiety of which can be substituted one or more times by $C_1$-$C_6$ alkyl, $C_1$-$C_6$ alkoxy, halogen, hydroxyl, trifluoromethyl, amino, acetylamino, nitrile, nitro or methylenedioxy, A is a straight-chained or branched, saturated or unsaturated aliphatic hydrocarbon chain containing up to 10 carbon atoms, which can be substituted one or more times by halogen or hydroxyl, and $R_1$ is a $C_1$-$C_8$ alkyl radical, which can be substituted one or more times by halogen, hydroxyl, nitrile, phenyl or carboxyl, or is a nitrile or formyl group, with the proviso that when R—A— is a methyl or ethyl radical, $R_1$ is not a methyl radical or a nitrile group and when R—A— is a benzyl radical, $R_1$ is not a methyl or benzyl radical; and the physiologically acceptable salts, carboxylic acid esters and amides thereof. The invention also provides processes for the preparation of these compounds pharmaceutical compositions containing them, and their use in combating hypoglycaemia.

10 Claims, No Drawings

PHARMACOLOGICALLY ACTIVE NOVEL O-SUBSTITUTED PYRUVIC ACID OXIMES

The present invention is concerned with new O-substituted pyruvic acid oximes and the physiologically acceptable salts, esters and amides thereof, as well as processes for the preparation thereof and the use thereof for combating diabetes mellitus, pre-diabetes, adipositas and atherosclerosis, as well as pharmaceutical compositions which contain these new compounds.

U.S. Pat. No. 4,136,196 describes hydrazones of pyruvic acid which have a hypoglycaemic action and contain phenelzine (2-phenylethyl hydrazine) and similar compounds as the hydrazine component. Several of the hydrazines hereby used are known to be monoaminooxidase inhibitors. In high doses, they can bring about hypoglycaemia (see P. I. Adnitt, Hypoglycaemic action of monoaminooxidase inhibitors, Diabetes, 17, 628-633/1980 etc.). The above-mentioned patent has the object of strengthening the hypoglycaemic effects of these hydrazines and, at the same time, of removing the undesired monoaminooxidase inhibition. This problem was solved by condensing the hydrazines with pyruvic acid.

Surprisingly, we have now found that pyruvic acid oximes and derivatives thereof which, as hydroxylamine components, contain O-alkylated hydroxylamines, possess valuable pharmacological properties which are not known to be possessed by the hydroxylamines upon which they are based. In contradistinction to the pyruvic acid hydrazones known from the literature, the new pyruvic acid oximes have a high chemical stability in physiological media.

In particular, the compounds according to the present invention inhibit the intestinal resorption of glucose. Furthermore, an outstanding hypoglycaemic action is observed. Therefore, the compounds are outstandingly suitable for the treatment of diseases in which, after the ingestion of carbohydrate-containing nutrients, a strong and long-lasting hyperglycaemia occurs. Thus, they can be used as therapeutic agents for indications such as diabetes mellitus, pre-diabetes, adipositas and atherosclerosis.

Consequently, according to the present invention, there are provided pyruvic acid oximes of the general formula:

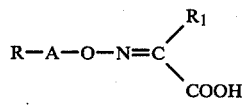  (I)

wherein R is a hydrogen atom or a $C_3$–$C_8$ cycloalkyl, $C_1$–$C_6$ alkoxy, cinnamyloxy, phenylamino, phenyl-N-alkylamino or phenylthio radical or an aryl or aryloxy radical, the aryl moiety of which can be substituted one or more times by $C_1$–$C_6$ alkyl, $C_1$–$C_6$ alkoxy, halogen, hydroxyl, trifluoromethyl, amino, acetylamino, nitrile, nitro or methylenedioxy, A is a straight-chained or branched, saturated or unsaturated aliphatic hydrocarbon chain containing up to 10 carbon atoms, which can be substituted one or more times by halogen or hydroxyl, and $R_1$ is a hydrogen atom, a $C_1$–$C_8$ alkyl radical, which can be substituted one or more times by halogen, hydroxyl, nitrile, phenyl or carboxyl, or is nitrile or formyl group, with the proviso that when R—A— is a methyl or ethyl radical, $R_1$ is not a methyl radical or a nitrile group and when R—A— is a benzyl radical, $R_1$ is not a methyl or benzyl radical; and the physiologically acceptable salts, carboxylic acid esters and amides thereof.

It is obvious that if R is an alkoxy or aryloxy radical, A must contain a straight-chained part with at least 2 carbon atoms by which the radical R is connected to the oxygen atom since otherwise acetals would be covered by general formula (I), acetals being unstable under physiological conditions.

In connection with the synthesis of α-amino acids, 2-ethoxyiminopropionic acid (general formula I; R=H; A=—$CH_2$—$CH_2$—) and 2-benzyloxyiminopropionic acid (general formula I; R=phenyl; A=—$CH_2$—) have been prepared as intermediates (see W. E. Weaver et al., J. Org. Chem., 15, 741/1950). 2-Methoxyiminopropionic acid (general formula I; R=H; A=—$CH_2$—) has been obtained in the case of making derivatives of pyruvic acid for analytical purposes (see Y. Ishitoya et al., Clin. Chim. Acta, 27, 233/1970). A pharmacodynamic action for these compounds has hitherto not been described so that the use thereof as pharmaceuticals is new.

Other known compounds are the methyl ester of cyanomethoxyiminoglyoxalic acid (see Beilstein, 3, I, p. 775) and 2-benzyloxyimino-3-phenylpropionic acid (see J. Org. Chem., 15, p. 741).

The cycloalkyl radical is to be understood to be a carbocycle containing 3 to 8 carbon atoms, the cyclohexyl radical being preferred.

The aryl radicals R are to be understood to be aromatic hydrocarbons containing 6 to 14 carbon atoms, the phenyl and naphthyl radical being preferred.

The substituted aryl radicals are to be understood to be aromatic hydrocarbons containing 6 to 14 carbon atoms which, in one or more positions, contain hydroxyl, halogen, trifluoromethyl, lower alkyl or lower alkoxy. The preferred aryl radicals are especially phenyl and naphthyl radicals substituted by the above-mentioned substituents. Halogen is to be understood to be fluorine, chlorine, bromine and iodine, fluorine, chlorine and bromine being preferred.

The lower alkyl radicals are to be understood to be, in all cases, straight-chained or branched radicals containing up to 6 carbon atoms, this definition also applying to the alkyl moieties of lower alkoxy radicals. The preferred lower alkyl radicals include the methyl and butyl radicals and the preferred lower alkoxy radical is the methoxy radical.

The aryloxy radicals contain aromatic hydrocarbon radicals having 6 to 14 carbon atoms, especially the phenyl radical.

In the case of unbranched alkylene chains A, there are, in all cases, preferably to be understood the following: —$(CH_2)_x$— in which X is 1 to 8, —CH=CH—$CH_2$— and —C≡C—$CH_2$—. The branched groups A are especially preferably the following:

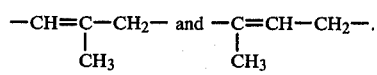

The physiologically acceptable salts are especially preferably the alkali metal, alkaline earth metal and ammonium salts, as well as possibly salts with blood sugar-lowering biguanides, the sodium salts being especially preferred.

The esters of the carboxylic acids of general formula (I) are generally to be understood, according to the present invention, to be the reaction products of the carboxylic acids with alcohols, the preferred alcohol components being the lower monohydroxy alcohols, such as methanol, ethanol, n-propanol and isopropanol.

The amides of general formula (I) according to the present invention contain, as amine component, for example ammonia and mono- and dialkylamines, for example 2-hydroxyethylamine and 1-methylpiperazine, as well as amino acids, examples of which include p-aminobenzoic acid, anthranilic acid, phenylalanine, α- and β-alanine, serine, valine, glycine, arginine and the like.

Preferred compounds according to the present invention include the 2-cinnamyloxyiminopropionic acid derivatives, the phenyl moiety of which can also be substituted. Pyruvic acid derivatives which carry a fluorine atom in the 3-position of the propionic acid are also preferred.

The present invention also includes all stereoisomeric forms of the compounds of general formula (I) which can occur because of asymmetric carbon atoms or double bonds (C=C or C=N) present in some of the compounds.

Furthermore, the present invention provides a process for the preparation of pyruvic acid oximes of general formula (I), wherein R, $R_1$ and A have the above-given meanings, in which, for example, (a) a hydroxylamine of the general formula:

R—A—O—NH$_2$     (II)

wherein R and A have the same meanings as above, is reacted in known manner with a compound of the general formula:

$$R_1-\underset{X'}{\overset{X}{C}}-COR'\quad\text{(III)}$$

wherein $R_1$ has the same meaning as above, X and X' are halogen atoms or alkoxy radicals or together represent an oxygen atom and R' is a hydroxyl group, a lower alkoxy radical or an optionally substituted amino group; or (b) a compound of the general formula:

R—A—Y     (IV)

wherein R and A have the same meanings as above and Y is a reactive group, is reacted in known manner with a compound of general formula (III), wherein X and X' together represent an =N—OH group and $R_1$ and R' have the same meanings as above; whereafter, if desired, an acid derivative obtained may be converted into the free acid or, if desired, a free acid obtained may be converted into an ester, an amide or a physiologically acceptable salt.

The halogen substituents X and X' in general formula (III) mean fluorine, chlorine, bromine or iodine and preferably chlorine or bromine. Alkoxy substituents X, X' and R' are radicals containing up to 4 carbon atoms, the methoxy and ethoxy radicals being preferred. As reactive compounds (IV) those are especially preferred in which Y is the anion of a strong acid, for example of a hydrohalic acid or sulphonic acid. It is preferred to use compounds of general formula (IV) in which Y is a p-toluenesulphonyloxy radical or a chlorine or bromine atom.

According to the above process (a), the substituted hydroxylamine (II) or a salt thereof is mixed in an appropriate polar solvent, for example water, a lower alcohol or acetic acid, with a compound of general formula (III) or preferably with a salt thereof and brought to a weakly acidic pH value, possibly with the help of a buffer, for example sodium acetate. The reaction can take place at ambient temperature but, for the purpose of accelerating the rate of the reaction, can also be carried out at an elevated temperature. The pyruvic acid oximes (I) formed can be filtered off from the reaction medium as sparingly soluble compounds or can be extracted with an appropriate non-polar solvent, for example diethyl ether or methylene chloride.

According to the above-mentioned process (b), a reactive compound (IV) is reacted in an appropriate polar solvent, for example a lower alcohol, with a compound of general formula (III), in which X and X' together represent an =N—OH group, with the addition of a basic condensation agent, for example an alkali metal hydroxide or alkali metal alcoholate, preferably at an elevated temperature. The pyruvic acid oximes can, possibly after neutralization of excess condensation agent, be extracted by appropriate solvents directly from the reaction mixture, for example by means of non-polar solvents, such as diethyl ether, or from the evaporation residues of the reaction mixture, for example by means of polar solvents, such as lower alcohols.

The preparation of the salts of the carboxylic acids of general formula (I) takes place in known manner, for example by reaction with appropriate free bases, carbonates or alcoholates.

The esters obtained as intermediates in the case of the above-described processes can be isolated and possibly directly saponified to give the corresponding carboxylic acids. On the other hand, when carboxylic acids are obtained, they can, again by known methods, be reacted to give the desired esters. The saponification of the esters is preferably carried out in an alkaline medium.

The amides of general formula (I) according to the present invention can be prepared by known methods from the carboxylic acids or from their reactive derivatives by reaction with amines.

Some of the substituted hydroxylamines and the salts thereof are new compounds. In general, it is not necessary to prepare them in pure form so the crude products obtained can be employed. They can be prepared by known processes, for example by reacting compounds of general formula (IV) with N-hydroxyphthalimide and subsequent splitting off of the phthalic acid protective group, for example by means of hydrazine, or with hydroxycarbamic acid esters and subsequent saponification of the O-alkylated derivatives.

As anti-diabetic compositions according to the present invention, there can be used all conventional oral and parenteral forms of administration, for example, tablets, capsules, dragees, syrups, solutions, suspensions, drops, suppositories and the like. For this purpose, the active material is mixed with solid or liquid carrier materials and subsequently brought into the desired form. Solid carrier materials include, for example, starch, lactose, methyl cellulose, talc, highly dispersed silicic acid, high molecular weight fatty acids (such as stearic acid), gelatine, agaragar, calcium phosphate, magnesium stearate, animal and vegetable fats and solid high molecular weight polymers (such as polyethylene glycols). Compositions suitable for oral administration can, if desired, contain flavoring and/or sweetening agents.

As injection medium, it is preferred to use water which contains the additives conventional for injection solutions, such as stabilizing agents, solubilizing agents and/or buffers. Additives of this kind include, for example, acetate and tartrate buffers, ethanol, complex formers (such as ethylenediamine-tetraacetic acid and the non-toxic salts thereof) and high molecular weight polymers (such as liquid polyethylene oxide) for viscosity regulation.

For combating diseases in which, after the ingestion of carbohydrate-containing nutriments, strong and long-lasting hyperglycaemia occurs, the pharmacologically active compounds of general formula (I) are administered in individual doses of 10 to 600 and preferably 50 to 200 mg., whereby these individual doses can, according to need, be administered one or more times per day.

Preferred compounds according to the present invention are, apart from those compounds mentioned in the following examples and the compounds which can be derived by combination of all meanings of the substituents given in the claims, also, in particular, the following acids, as well as the salts, esters and amides thereof:

2-(3,5-di-tert.-butyl-4-hydroxycinnamyloxyimino)-propionic acid;
2-(2-n-propoxycinnamyloxyimino)-propionic acid;
2-(5-chloro-3-methylcinnamyloxyimino)-propionic acid.

The following examples are given for the purpose of illustrating the present invention:

EXAMPLE 1

Sodium 2-(2-methallyloxyimino)-propionate 10.3 g. (0.1 mol) Pyruvic acid oxime are first introduced, with stirring, into a solution of 13.6 g. (0.2 mol) sodium ethylate in 200 ml. ethanol. Subsequently, at boiling temperature, 18.1 g. (0.2 mol) β-methallyl chloride are added dropwise thereto and the reaction maintained at this temperature for 14 hours. A further 9.0 g. (0.1 mol) β-methallyl chloride and 6.8 g. (0.1 mol) sodium ethylate are now added and heating continued for another 7 hours. The resultant precipitate is filtered off with suction from the hot reaction mixture and the filtrate is evaporated. The evaporation residue is recrystallized from ethanol to give 7.3 g. (61% of theory) sodium 2-(2-methallyloxyimino)-propionate; m.p. 240° C. (decomp.).

In an analogous manner, there is obtained from pyruvic acid oxime and
 (a) 2-methoxyethyl bromide sodium 2-(2-methoxyethyloxyimino)-propionate m.p. 185° C. (decomp.)
 (b) 3-phenylpropyl bromide sodium 2-(3-phenyl-propyloxyimino)-propionate m.p. 234° C. (decomp.) (recrystallized from aqueous ethanol)
 (c) 2-phenoxyethyl bromide sodium 2-(2-phenoxyethyloxyimino)-propionate m.p. 209° C. (decomp.) (recrystallized from ethanol)
 (d) 2-cyclohexylethyl bromide sodium 2-(2-cyclohexylethyloxyimino)-propionate m.p. 234°-235° C. (decomp.) (recrystallized from ethanol).

EXAMPLE 2

2-(2-p-Tolyethyloxyimino)-propionic acid 2-p-Tolylethyl bromide and pyruvic acid oxime are reacted by the process of Example 1 and the reaction mixture is evaporated when the reaction is complete. The residue is taken up in a little water, washed with diethyl ether and the aqueous solution is acidified. The precipitate obtained is filtered off with suction and dried to give a yield of 41% of theory of 2-(2-p-tolylethyloxyimino)-propionic acid; m.p. 106°-108° C.

In an analogous manner, there is obtained from pyruvic acid oxime and
 (a) 2-phenylethyl bromide 2-(2-phenylethyloxyimino)-propionic acid m.p. 74° C.
 (b) hexyl bromide 2-hexyloxyimino propionic acid m.p. 41° C.
 (c) octyl bromide 2-octyloxyiminopropionic acid m.p. 42° C. (recrystallized from ligroin)
 (d) 3-phenylpropargyl bromide 2-(3-phenyl-2-propynyloxyimino)-propionic acid m.p. 84°-85° C.

EXAMPLE 3

2-(γ-Methylcinnamyloxyimino)-propionic acid

A suspension of 4.2 g. (21 mmol) O-(γ-methylcinnamyl)-hydroxylamine hydrochloride in 50 ml. water is covered with 50 ml. methylene chloride and subsequently mixed, while stirring, with a solution of 2.73 g. (31 mmol) pyruvic acid and 2.54 g. (31 mmol) sodium acetate in 10 ml. water, the precipitate thereby largely dissolving. The reaction mixture is further stirred for 1 hour, the methylene chloride phase is separated off and the aqueous phase is extracted with methylene chloride. The combined organic extracts are dried and evaporated. The residue is recrystallized from ligroin to give 3.3 g. (67% of theory) 2-(γ-methylcinnamyloxyimino)-propionic acid; m.p. 56°-58° C.

In an analogous manner, there is obtained from pyruvic acid and
 (a) O-cinnamylhydroxylamine hydrochloride 2-cinnamyloxyiminopropionic acid m.p. 89°-91° C.
 (b) O-(β-methylcinnamyl)-hydroxylamine hydrochloride 2-(β-methylcinnamyloxyimino)-propionic acid m.p. 139° C.

EXAMPLE 4

2-(3-Chlorocinnamyloxyimino)-propionic acid

A solution of 5.6 g. (64 mmol) pyruvic acid in 100 ml. water is added dropwise at ambient temperature, while stirring, to a solution of 7.8 g. (42 mmol) O-(3-chlorocinnamyl)-hydroxylamine in 100 ml. methylene chloride. The reaction mixture is then stirred for 15 minutes, the organic phase is separated off and the aqueous phase is again extracted with methylene chloride. The combined methylene chloride solutions are dried and evaporated and the residue obtained is recrystallized from a mixture of ethyl acetate and ligroin to give a yield of 8.4 g. (78% of theory) 2-(3-chlorocinnamyloxyimino)-propionic acid; m.p. 99°-101° C.

In an analogous manner, there is obtained from pyruvic acid and
 (a) O-(2-chlorocinnamyl)-hydroxylamine 2-(2-chlorocinnamyloxyimino)-propionic acid m.p. 88°-90° C. (recrystallized from aqueous methanol)
 (b) O-(4-chlorocinnamyl)-hydroxylamine 2-(4-chlorocinnamyloxyimino)-propionic acid m.p.

114°–116° C. (recrystallized from ethyl acetate-ligroin)

(c) O-allylhydroxylamine 2-(allyloxyimino)-propionic acid m.p. 38°–39° C.

EXAMPLE 5

2-(4-Fluorocinnamyloxyimino)-propionic acid 8.2 g. (49 mmol) O-(4-Fluorocinnamyl)-hydroxylamine are reacted with 5.2 g. (59 mmol) pyruvic acid by the process of Example 4 to give 6.2 g. (53% of theory) 2-(4-fluorocinnamyloxyimino)-propionic acid; m.p. 98°–100° C. (recrystallized from ethyl acetate and ligroin).

In an analogous manner, there is obtained from pyruvic acid and (a) O-(3-trifluoromethylcinnamyl)-hydroxylamine 2-(3-trifluoromethylcinnamyloxyimino)-propionic acid m.p. 103°–105° C.
(b) O-(3-methylcinnamyl)-hydroxylamine 2-(3-methylcinnamyloxyimino)-propionic acid sodium salt: m.p. 240° C. (decomp.)
(c) O-(4-tert.-butylcinnamyl)-hydroxylamine 2-(4-tert.-butylcinnamyloxyimino)-propionic acid m.p. 114°–116° C.
(d) O-(3-methoxycinnamyl)-hydroxylamine 2-(3-methoxycinnamyloxyimino)-propionic acid m.p. 91°–92° C.
(e) O-(2-methoxycinnamyl)-hydroxylamine 2-(2-methoxycinnamyloxyimino)-propionic acid m.p. 84°–86° C.
(f) O-(5-chloro-2-methylcinnamyl)-hydroxylamine 2-(5-chloro-2-methylcinnamyloxyimino)-propionic acid m.p. 112° C.
(g) O-(5-chloro-2-methoxycinnamyl)-hydroxylamine 2-(5-chloro-2-methoxycinnamyloxyimino)-propionic acid m.p. 124°–126° C.
(h) O-[3-(1-naphthyl)-2-propenyl]-hydroxylamine 2-[3-(1-naphthyl)-2-propenyloxyimino]-propionic acid m.p. 85°–87° C.
(i) O-(3,5-dichlorocinnamyl)-hydroxylamine 2-(3,5-dichlorocinnamyloxyimino)-propionic acid m.p. 101°–104° C.
(j) O-(5-chloro-2-methoxy-β-methylcinnamyl)-hydroxylamine 2-(5-chloro-2-methoxy-β-methylcinnamyloxyimino)-propionic acid m.p. 108°–110° C.
(k) O-(5-bromo-2-methoxycinnamyl)-hydroxylamine 2-(5-bromo-2-methoxycinnamyloxyimino)-propionic acid m.p. 118°–120° C.
(l) O-(5-fluoro-2-methoxycinnamyl)-hydroxylamine 2-(5-fluoro-2-methoxycinnamyloxyimino)-propionic acid m.p. 114°–116° C.
(m) O-(2-methoxy-5-trifluoromethylcinnamyl)-hydroxylamine 2-(2-methoxy-5-trifluoromethylcinnamyloxyimino)-propionic acid m.p. 120°–123° C.
(n) O-(2,5-dimethoxycinnamyl)-hydroxylamine 2-(2,5-dimethoxycinnamyloxyimino)-propionic acid m.p. 74°–76° C.
(o) O-(2-methoxy-5-methylcinnamyl)-hydroxylamine 2-(2-methoxy-5-methylcinnamyloxyimino)-propionic acid m.p. of the sodium salt 218° C.

EXAMPLE 6

Ethyl 2-(cinnamyloxyimino)-propionate

A mixture of 2.2 g. (10 mmol) 2-(cinnamyloxyimino)-propionic acid, 16 ml. chloroform, 1.78 g. (15 mmol) thionyl chloride and 2 drops of dimethylformamide is heated under reflux for 2 hours. The chloroform and excess thionyl chloride are then evaporated off under vacuum. The oil remaining behind is mixed with 20 ml. ethanol and left to stand for 12 hours at ambient temperature. The ethanol is then evaporated in a vacuum and the residue taken up in diethyl ether. The solution is washed twice with a saturated aqueous solution of sodium bicarbonate, dried and evaporated in a vacuum. The residue is dissolved in ligroin, clarified with charcoal and again evaporated. As residue, there are obtained 2.4 g. (97% of theory) ethyl 2-(cinnamyloxyimino)-propionate in the form of a colorless oil; $n_D^{20} = 1.5390$.

EXAMPLE 7

2-(Cinnamyloxyimino)-propionamide 2-(Cinnamyloxyimino)-propionyl chloride is prepared from 4.38 g. (20 mmol) 2-(cinnamyloxyimino)-propionic acid and 3.57 g. (30 mmol) thionyl chloride in the manner described in Example 6. The crude acid chloride is dissolved in 20 ml. chloroform and added, while stirring, to an ice-cooled solution of ammonia in 40 ml. chloroform. The reaction mixture is left to stand overnight at ambient temperature and then shaken up with 100 ml. water. Subsequently, the organic phase is first washed with 0.5 N hydrochloric acid, then with a saturated aqueous solution of sodium bicarbonate and dried over anhydrous sodium sulphate and evaporated in a vacuum. The residue is recrystallized from a mixture of ethyl acetate and ligroin to give 2.9 g. (66% of theory) 2-(cinnamyloxyimino)-propionamide; m.p. 120°–121° C.

In an analogous manner, from 2-(cinnamyloxyimino)-propionyl chloride and ethanolamine, there is obtained: 2-(cinnamyloxyimino)-propionic acid N-(2-hydroxyethylamide); m.p. 74°–76° C.

EXAMPLE 8

4-[2-(Cinnamyloxyimino)-propionyl]-1-methylpiperazine 4.8 g. (20 mmol) 2-(cinnamyloxyimino)-propionyl chloride (prepared according to Example 6) are added dropwise, while stirring, at 0° C. to a solution of 2.0 g. (20 mmol) 1-methylpiperazine in 40 ml. dry pyridine and the reaction mixture is further stirred for 1 hour at 0° C. and then poured on to ice. The reaction mixture is extracted with diethyl ether and the ether extracts are dried over anhydrous sodium sulphate and evaporated. There are obtained 4.3 g. (71% of theory) 4-[2-(cinnamyloxyimino)-propionyl]-1-methylpiperazine in the form of a colorless oil. The hydrochloride, (recrystallized from isopropanol) melts at 162°–164° C.

In an analogous manner, from β-alanine ethyl ester hydrochloride and 2-(cinnamyloxyimino)-propionyl chloride, there is obtained ethyl 3-[2-(cinnamyloxyimino)-propionylamido]-propionate in the form of a colorless oil.

13.7 g. (43 mmol) of the crude ester are dissolved in 250 ml. methanol and mixed with 90 ml. 1 N aqueous potassium hydroxide solution. The reaction mixture is heated, while stirring, for 2 hours at 40° C., whereafter the methanol is distilled off in a vacuum. The aqueous residue is clarified with charcoal and neutralized with 90 ml. of 1 N hydrochloric acid. The precipitated crystals are filtered off with suction and recrystallized from a mixture of ethyl acetate and ligroin. There are obtained 7.3 g. (58% of theory) 3-[2-(cinnamyloxyimino)-propionylamido]-propionic acid; m.p. 111°–113° C.

EXAMPLE 9

2-(Cinnamyloxyimino)-3-fluoropropionic acid

A solution of 4.82 g. (33 mmol) sodium 3-fluoro-2-oxopropionate hydrate in 50 ml. water is added dropwise, while stirring, to a solution of 4.1 g. (27.5 mmol) O-cinnamylhydroxylamine in 50 ml. methylene chloride. The mixture is then mixed with 33 ml. (33 mmol) 1 N hydrochloric acid, further stirred for 30 minutes and the organic phase separated off. It is washed with water, dried over anhydrous sodium sulphate and evaporated. The residue is recrystallized twice from ethyl acetate and ligroin. There are obtained 3.1 g. (48% of theory) 2-(cinnamyloxyimino)-3-fluoropropionic acid; m.p. 81°–83° C.

In an analogous manner, from 3-chloro-2-oxopropionic acid and O-cinnamylhydroxylamine, there is obtained 3-chloro-2-cinnamyloxyiminopropionic acid; m.p. 95°–98° C.

EXAMPLE 10

Cinnamyloxyiminoacetic acid

A solution of 3.73 g. (25 mmol) O-cinnamylhydroxylamine in 50 ml. methylene chloride is mixed, while stirring, with a solution of 2.22 g. (30 mmol) glyoxylic acid in 50 ml. water and the reaction mixture stirred for 30 minutes at ambient temperature. The phases are then separated and the organic phase is washed with water, dried with anhydrous sodium sulphate and evaporated. The residue is recrystallized from ethyl acetate and ligroin to give 2.7 g. (53% of theory) cinnamyloxyiminoacetic acid; m.p. 85°–88° C.

In an analogous manner, there is obtained from O-cinnamylhydroxylamine and
- (a) 2-oxobutyric acid 2-cinnamyloxyiminobutyric acid m.p. 75°–77° C.
- (b) 3-methyl-2-oxobutyric acid 2-cinnamyloxyimino-3-methylbutyric acid sodium salt: m.p. 220° C. (decomp.)
- (c) 2-oxovaleric acid 2-cinnamyloxyiminovaleric acid m.p. 53°–55° C.
- (d) 4-methyl-2-oxovaleric acid 2-cinnamyloxyimino-4-methylvaleric acid m.p. 60°–62° C.
- (e) 3-methyl-2-oxovaleric acid 2-cinnamyloxyimino-3-methylvaleric acid m.p. 57°–59° C.
- (f) 2-oxooctanoic acid 2-cinnamyloxyiminooctanoic acid m.p. 56°–58° C.
- (g) phenylpyruvic acid 2-cinnamyloxyimino-3-phenylpropionic acid m.p. 84°–86° C.
- (h) oxalacetic acid 2-cinnamyloxyiminosuccinic acid m.p. 124°–126° C.
- (i) α-ketoglutaric acid 2-cinnamyloxyiminoglutaric acid m.p. 121°–123° C.

EXAMPLE 11

Sodium 2-(4-phenylbutoxyimino)-propionate

A solution of 5.0 g. (30 mmol) O-(4-phenylbutyl)-hydroxylamine in 60 ml. methylene chloride is mixed dropwise, while stirring, with a solution of 9.2 g. (36 mmol) pyruvic acid in 60 ml. water. The reaction mixture is stirred for 30 minutes and the phases then separated. The organic phase is dried over anhydrous sodium sulphate and evaporated in a vacuum. As residue, there are obtained 7.1 g. of a colorless oil which, upon treating with a solution of 2.3 g. (27.5 mmol) sodium bicarbonate in 50 ml. water, dissolves with foaming. The aqueous solution is washed with diethyl ether, clarified with charcoal and evaporated in a vacuum. The residue is then triturated with acetone to give 4.0 g. (52% of theory) sodium 2-(4-phenylbutoxyimino)-propionate; m.p. 215°–216° C.

In an analogous manner, there are obtained from pyruvic acid and
- (a) O-(5-phenylpentyl)-hydroxylamine sodium 2-(5-phenylpentoxyimino)-propionate m.p. 209°–212° C.
- (b) O-(2-phenoxypropyl)-hydroxylamine sodium 2-(2-phenoxypropoxyimino)-propionate m.p. 204°–206° C.

EXAMPLE 12

2-(3-Phenoxypropoxyimino)-propionic acid 5.0 g. (30 mmol) O-(3-phenoxypropyl)-hydroxylamine are reacted with 3.2 g. (36 mmol) pyruvic acid by the process according to Example 11 and the evaporation residue is recrystallized from ethyl acetate and ligroin. There are obtained 6.1 g. (86% of theory) 2-(3-phenoxypropoxyimino)-propionic acid; m.p. 86°–88° C.

In an analogous manner, from pyruvic acid and O-[2-(4-chlorophenoxy)-propyl]-hydroxylamine, there is obtained 2-[2-(4-chlorophenoxy)-propoxyimino]-propionic acid; m.p. 70°–73° C.

EXAMPLE 13

2-Cinnamyloxyiminopropionic acid 4.0 g. (28 mmol) O-Cinnamylhydroxylamine are added to a solution of 3.5 g. (24 mmol) 2,2-dichloropropionic acid and 3.45 g. (25 mmol) potassium carbonate in 40 ml. water. The reaction mixture is heated, while stirring, to 90° C. and, within the course of 30 minutes, a solution of a further 3.5 g. (25 mmol) potassium carbonate in 15 ml. water added thereto, followed by stirring for 1 hour at 90° C. The reaction mixture is then cooled, shaken out with diethyl ether and acidified with hydrochloric acid. The precipitate obtained is filtered off with suction and recrystallized from a mixture of ligroin and ethyl acetate. There are obtained 3.0 g. (57% of theory) 2-cinnamyloxyiminopropionic acid; m.p. 89°–91° C.

The mixed melting point with the product described in Example 3a shows no depression.

EXAMPLE 14

Methyl 2-cinnamyloxyiminopropionate 2.8 g. (15 mmol) O-cinnamylhydroxylamine hydrochloride in 20 ml. water are added to 2.8 g. (19 mmol) methyl 2,2-dimethoxypropionate in 100 ml. water. The mixture is left to stand for 2 days, with occasional shaking, and the resultant oil then extracted with methylene chloride. The extracts are dried and evaporated. As residue, there are obtained 3.3 g. (94% of theory) methyl 2-cinnamyloxyiminopropionate in the form of a colorless oil.

The ester can be saponified with a methanolic solution of potassium hydroxide to give 2-cinnamyloxyiminopropionic acid; m.p. 89°–91° C.

EXAMPLE 15

2-(3-Fluorocinnamyloxyimino)-pyruvic acid 6.2 g. (37 mmol) O-(3-fluorocinnamyl)-hydroxylamine are reacted with 3.9 g. (44 mmol) pyruvic acid by the process of Example 4 to give 5.4 g. (61% of theory) 2-(3-fluorocinnamyloxyimino)-pyruvic acid; m.p. 88°–90° C., after recrystallization from ethyl acetate and ligroin.

The following compounds can be prepared in an analogous manner by appropriate choice of starting materials:

2-[3-(3-methylphenyl)-propoxyimino]-propionic acid
2-[3-(4-methylphenyl)-propoxyimino]-propionic acid
2-[3-(3-chlorophenyl)-propoxyimino]-propionic acid
2-[3-(4-chlorophenyl)-propoxyimino]-propionic acid
2-[3-(3-methoxyphenyl)-propoxyimino]-propionic acid
2-[3-(4-methoxyphenyl)-propoxyimino]-propionic acid
2-(2-methyl-3-phenylpropoxyimino)-propionic acid
2-[5-(3-chlorophenyl)-pentyloxyimino]-propionic acid
2-[5-(4-chlorophenyl)-pentyloxyimino]-propionic acid
2-[5-(4-methoxyphenyl)-pentyloxyimino]-propionic acid
2-(3-cyclohexyl-2-propenyloxyimino)-propionic acid
2-(4-methylcinnamyloxyimino)-propionic acid
2-(3-t-butylcinnamyloxyimino)-propionic acid
2-(3-bromocinnamyloxyimino)-propionic acid; m.p. 107°–109° C.
2-(3-cyanocinnamyloxyimino)-propionic acid
2-(3,4-methylenedioxycinnamyloxyimino)-propionic acid
2-(3-nitrocinnamyloxyimino)-propionic acid; m.p. 131°–132° C.
2-(3-aminocinnamyloxyimino)-propionic acid
2-(3-acetamidocinnamyloxyimino)-propionic acid
2-[3-(3-methylphenyl)-2-propynyloxyimino]-propionic acid
2-[3-(4-methylphenyl)-2-propynyloxyimino]-propionic acid
2-[3-(3-chlorophenyl)-2-propynyloxyimino]-propionic acid
2-[3-(4-chlorophenyl)-2-propynyloxyimino]-propionic acid
2-[3-(4-methoxyphenyl)-2-propynyloxyimino]-propionic acid
2-(3-hydroxy-3-phenylpropoxyimino)-propionic acid
2-(2-hydroxy-3-phenylpropoxyimino)-propionic acid
2-(2-chloro-3-phenylpropoxyimino)-propionic acid
2-(β-chlorocinnamyloxyimino)-propionic acid; m.p. 116°–118° C.
2-(3-oxo-3-phenylpropoxyimino)-propionic acid
2-(2-oxo-3-phenylpropoxyimino)-propionic acid
2-[2-(3-chlorophenoxy)-propoxyimino]-propionic acid
2-[2-(4-methoxyphenoxy)-propoxyimino]-propionic acid
2-[3-(3-chlorophenoxy)-propoxyimino]-propionic acid
2-[3-(4-chlorophenoxy)-propoxyimino]-propionic acid
2-[3-(4-methoxyphenoxy)-propoxyimino]-propionic acid
2-(2-hydroxy-3-phenoxypropoxyimino)-propionic acid
2-(3-anilinopropoxyimino)-propionic acid
2-[3-(N-methylanilino)-propoxyimino]-propionic acid
2-(3-anilino-2-hydroxypropoxyimino)-propionic acid
2-(3-phenylthiopropoxyimino)-propionic acid
2-(2-cinnamyloxyethoxyimino)-propionic acid
3-fluoro-2-(2-propenyloxyimino)-propionic acid
2-(2-propenyloxyimino)-butyric acid
3-fluoro-2-hexyloxyiminopropionic acid
2-(2-hexyloxyimino)-butyric acid; m.p. 236°–237° C. (Na salt)
3-hydroxy-2-(3-phenylpropoxyimino)-propionic acid
3-fluoro-2-(3-phenylpropoxyimino)-propionic acid
2-(3-phenylpropoxyimino)-butyric acid
2-[3-(3-chlorophenyl)-propoxyimino]-3-fluoropropionic acid
2-[3-(3-chlorophenyl)-propoxyimino]-butyric acid
3-fluoro-2-[3-(3-methylphenyl)-propoxyimino]-propionic acid
2-[3-(3-methylphenyl)-propoxyimino]-butyric acid
3-oxo-2-cinnamyloxyimino-propionic acid
2-cinnamyloxyimino-3,3-dichloropropionic acid
2-cinnamyloxyimino-3-cyanopropionic acid
2-cinnamyloxyimino-4-cyanobutyric acid
2-cinnamyloxyimino-3-hydroxypropionic acid
2-(3-chlorocinnamyloxyimino)-3-fluoropropionic acid; m.p. 92°–94° C.
2-(3-chlorocinnamyloxyimino)-butyric acid; m.p. 91°–93° C.
3-fluoro-2-(3-methylcinnamyloxyimino)-propionic acid
2-(3-methylcinnamyloxyimino)-butyric acid
3-hydroxy-2-(3-phenylpropyn-2-yloxyimino)-propionic acid
3-fluoro-2-(3-phenylpropyn-2-yloxyimino)-propionic acid
2-(3-phenylpropyn-2-yloxyimino)-butyric acid
2-[3-(3-chlorophenyl)-propyn-2-yloxyimino]-3-fluoropropionic acid
2-[3-(3-chlorophenyl)-propyn-2-yloxyimino]-butyric acid
3-fluoro-2-[3-(3-methylphenyl)-propyn-2-yloxyimino]-propionic acid
2-[3-(3-methylphenyl)-propyn-2-yloxyimino]-butyric acid
3-fluoro-2-(2-phenoxypropoxyimino)-propionic acid
2-(2-phenoxypropoxyimino)-butyric acid.

The novel compounds may be administered by themselves or in conjunction with carriers which are pharmacologically acceptable, either active or inert. The dosage units are about 0.2 to 2 grams per day for an adult or about 3–30 mg/kg per day although higher or lower dosages can be used. Rather than a single dose it is preferable if the compounds are administered in the course of a day, i.e. about four applications of 100 mg. each at spaced time intervals or 8 of about 50 mg. each. A convenient form of administration is in a gelatine capsule.

The dosage of the novel compounds of the present invention for the treatment of diabetes depends in the main on the age, weight, and condition of the patient being treated. The preferable form of administration is via the oral route in connection with which dosage units containing 50–500 mg. of active compound in combination with a suitable pharmaceutical diluent is employed. One or two unit dosages are good from one to four times a day.

For the preparation of pharmaceutical compositions, at least one of the new compounds (I) is mixed with a solid or liquid pharmaceutical carrier or diluent and optionally with an odoriferous, flavoring and/or coloring material and formed, for example, into tablets or dragees, or with the addition of appropriate adjuvants, suspended or dissolved in water or in an oil, for example, olive oil.

The compounds (I) can be administered orally or parenterally in liquid or solid form. As injection medium, it is preferred to use water which contains the stabilizing agents, solubilizing agents and/or buffers, conventional for injection solutions. Additives of this type include, for example, tartrate and borate buffers, ethanol, dimethyl sulphoxide, complex-forming agents (such as ethylene diaminetetraacetic acid), high molecular weight polymers (such as liquid polyethylene oxide) for viscosity regulation or polyoxyethylene derivatives of sorbitan anhydrides.

As noted hereinabove the material administered may be the acid or a salt, ester or amide thereof. It is believed that due to hydrolysis in the body the active material is in all these instances the same, viz. probably the acid.

1. Test procedure for determination of threshold dose

Fasting guinea pigs were used as experimental models to determine the threshold dose of the blood-glucose-lowering activity of the substances to be investigated. Food was withheld from the animals used in the investigations for 16 hours prior to the start of the tests. The animals remained without food for the entire testing period but had free access to drinking water.

The substances were administered intraperitoneally as a solution of the potassium salt at pH 7.4.

A parallel control group was given an 0.9% NaCl solution.

The drawing of blood for determination of the glucose concentrations was effected immediately prior to administration of the substances and at one-hour intervals up to the fourth hour after the administration of the substances. To this end, an ear vein was carefully punctured with a No. 18 cannula, and the drops of blood issuing were picked up with a 10 µl capillary.

The blood-glucose concentration was determined in the hemolyzate by the specific hexokinase method. To this end, the 10 µl blood sample was pipetted into a stabilizer solution containing digitonin as hemolysis accelerator and maleinimide as glucose inhibitor. Following this, an aliquot was taken from the hemolyzate so obtained and determined by the hexokinase method on an LKB 8600 (made by LKB, Bromma, Sweden).

The dose which with the specified number of test animals per dose group (N=4) was just large enough to produce a significant lowering of fasting glycemia (p>0.05) was adopted as threshold dose.

2. Test procedure for determination of resorption-inhibiting activity

To determine the effect on glucose resorption, oral glucose loading was effected. To this end, the substance to be tested was administered intraperitoneally as potassium salt, as described, to a group of ten fasting guinea pigs. At the same time, 1 g glucose was orally administered to the animals as a 20% solution by means of an esophageal bougie.

After a preliminary value had been established, blood was taken from the animals at close intervals (20 min. to 200 min.) for determination of the glucose concentrations, as described.

A parallel control group was also given 1 g glucose p. o., and intraperitoneally a corresponding amount of 0.9% NaCl solution.

The blood-glucose concentration was determined in the hemolyzate by the hexokinase method, as described.

With regard to glucose resorption, the area under the concentration/time curve, calculated by means of the empirical trapeze formula, served as quantity to be measured. The difference in the area between the control and test groups, expressed in percent, was used as a measure for the inhibition of glucose resorption.

The results obtained were as follows:

| Example | Threshold dose Guinea pigs (mg/kg) i.p. | Resorption inhibition Dose (mg/kg) i.p. | % inhibition |
|---|---|---|---|
| 1c | 50 weak | 40 | 25 |
| 1b | 25–50 | 20 | 39 |
| 3 | 50 | 30 | 0 |
| 4b | 25–50 flat D-W curve | 20 | 10 |
| 4a | 50 weak | 40 | 41 |
| 4 | 25 | 20 | 55 |
| 4c | >50 | 40 | 37 |
| 2d | 25 wk. indiv. animals | 40 | 65 |
| 5D | 25 | 25 | 36 |
| 5 | 50 | 40 | 3 |
| 5a | 50 | 40 | 34 |
| 5f | 50 | 40 | 33 |
| 9 | 25 | 20 | 26 |
| 10a | 25 | 20 | 0 |
| 8 | >50 | 40 | 44 |
| 3a | 25 | 10 | 33 |
| 2a | 75 | 40 | 33 |
| 3b | 50 | 40 | 40 |
| 10 | >50 | 25 | 69 |

It will be appreciated that the instant specification and examples are set forth by way of illustration and not limitation, and that various modifications and changes may be made without departing from the spirit and scope of the present invention.

We claim:

1. A pyruvic acid oxime of the formula

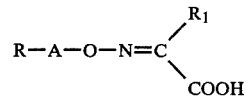

wherein

R is a hydrogen atom, or a $C_3$–$C_8$ cycloalkyl, methoxy, cinnamyloxy, phenylamino, phenyl-N-methylamino or phenylthio radical, or an aryl or aryloxy radical of which the aryl moiety is phenyl or naphthyl and can be substituted one or more times by $C_1$–$C_6$ alkyl, $C_1$–$C_6$ alkoxy, halogen, hydroxyl, trifluoromethyl, amino, acetylamino, nitrile, nitro or methylenedioxy, A is a straight-chained or branched, saturated or unsaturated aliphatic hydrocarbon chain containing 2 to 8 carbon atoms, which can be substituted by a halogen or hydroxyl-group, and $R_1$ is a hydrogen atom, a $C_1$–$C_6$ alkyl radical which can be substituted one or two times by halogen, hydroxyl or phenyl, with the proviso that R—A— is not a saturated alkyl radical with 2-4 C-atoms, or a physiologically compatible salt, carboxylic acid $C_7$–$C_6$-alkyl esters or amide, mono- or dialkylamide, the alkyl groups having 1 to 6 carbon atoms, and carboxy alkylamide of naturally occurring amino acids thereof.

2. A compound, salt, ester or amide according to claim 1, wherein A is a —$CH_2$—$CH_2$—, —$CH_2$—$CH_2$—$CH_2$—, —CH=CH—$CH_2$,

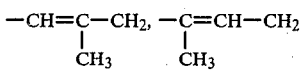

or —C≡C—CH$_2$-radical, and R$_1$ is a methyl, ethyl or fluoromethyl radical.

3. A compound according to claim 1, wherein such compound is 2-(2-phenylethyloxyimino)-propionic acid of the formula

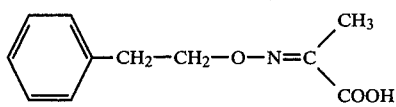

or a physiologically compatible salt thereof.

4. A compound according to claim 1, wherein such compound is 2-cinnamyloxyiminopropionic acid of the formula

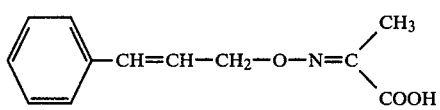

or a physiologically compatible salt thereof.

5. A compound according to claim 1, wherein such compound is 2-(β-methylcinnamyloxyimino)-propionic acid of the formula

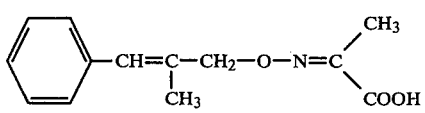

or a physiologically compatible salt thereof.

6. A compound according to claim 1, wherein such compound is 2-(3-chlorocinnamyloxyimino)-propionic acid of the formula

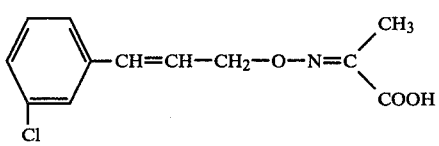

or a physiologically compatible salt thereof.

7. A compound according to claim 1, wherein such compound is 2-(cinnamyloxyimino)-3-fluoropropionic acid of the formula

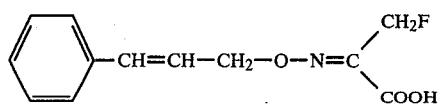

or a physiologically compatible salt thereof.

8. A hypoglycaemic composition of matter comprising a hypoglycaemically active amount of a compound according to claim 1 or a salt, ester or amide thereof in admixture with a diluent.

9. A method of lowering the blood sugar level of a patient comprising administering to such patient a hypoglycaemically active amount of a pyruvic acid oxime of the formula

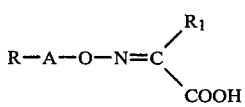

wherein

R is a hydrogen atom, or a C$_3$-C$_8$ cycloalkyl, methoxy, cinnamyloxy, phenylamino, phenyl-N-methylamino or phenylthio radical, or an aryl or aryloxy radical of which the aryl moiety is phenyl or naphthyl and can be substituted one or more times by C$_1$-C$_6$ alkyl, C$_1$-C$_6$ alkoxy, halogen, hydroxyl, trifluoromethyl, amino, acetylamino, nitrile, nitro or methylenedioxy, A is a straight-chained or branched, saturated or unsaturated aliphatic hydrocarbon chain containing up to 8 carbon atoms, which can be substituted by a halogen or hydroxyl-group, and R$_1$ is a hydrogen atom, C$_1$-C$_6$ alkyl radical which can be substituted one or two times by halogen, hydroxyl or phenyl, with the proviso that R—A— is not a methyl or ethyl or benzyl radical, or a physiologically compatible salt, carboxylic acid C$_1$-C$_6$ alkyl ester or amide, mono- or dialkylamide, the alkyl groups having 1-6 carbon atoms and carboxy alkylamide of naturally occurring aminoacids thereof.

10. The method according to claim 9, wherein there is administered
2-(2-phenylethyloxyimino)-propionic acid,
2-cinnamyloxyiminopropionic acid,
2-(β-methylcinnamyloxyimino)-propionic acid,
2-(3-chlorocinnamyloxyimino)-propionic acid, or
2-(cinnamyloxyimino)-3-fluoropropionic acid,
or a physiologically compatible salt thereof.

* * * * *